United States Patent
Rosser et al.

(10) Patent No.: US 11,464,921 B2
(45) Date of Patent: Oct. 11, 2022

(54) CARTRIDGES FOR VAPORIZER DEVICES

(71) Applicant: JUUL Labs, Inc., San Francisco, CA (US)

(72) Inventors: Christopher James Rosser, Cambridge (GB); Simon J. Smith, Hertford (GB)

(73) Assignee: JUUL Labs, Inc., San Francisco, CA (US)

( * ) Notice: Subject to any disclaimer, the term of this patent is extended or adjusted under 35 U.S.C. 154(b) by 339 days.

(21) Appl. No.: 16/674,476

(22) Filed: Nov. 5, 2019

(65) Prior Publication Data
US 2020/0138113 A1    May 7, 2020

Related U.S. Application Data

(60) Provisional application No. 62/755,886, filed on Nov. 5, 2018.

(51) Int. Cl.
| | |
|---|---|
| A24F 13/00 | (2006.01) |
| A24F 17/00 | (2006.01) |
| A24F 25/00 | (2006.01) |
| A61M 11/04 | (2006.01) |

(52) U.S. Cl.
CPC ................. A61M 11/042 (2014.02)

(58) Field of Classification Search
CPC ........ A24F 40/10; A24F 40/42; A61M 11/042
See application file for complete search history.

(56) References Cited

U.S. PATENT DOCUMENTS

| | | |
|---|---|---|
| 4,797,692 A | 1/1989 | Ims |
| 4,990,939 A | 2/1991 | Sekiya et al. |
| 6,196,218 B1 | 3/2001 | Voges |
| 6,722,763 B1 | 4/2004 | Hsu et al. |
| 6,909,840 B2 | 6/2005 | Harwig et al. |
| 7,766,013 B2 | 8/2010 | Wensley et al. |
| 7,845,359 B2 | 12/2010 | Montaser |

(Continued)

FOREIGN PATENT DOCUMENTS

| | | |
|---|---|---|
| CN | 104102143 A | 10/2014 |
| CN | 107889450 A | 4/2018 |

(Continued)

*Primary Examiner* — Abdullah A Riyami
*Assistant Examiner* — Thang H Nguyen
(74) *Attorney, Agent, or Firm* — Mintz Levin Cohn Ferris Glovsky and Popeo, P.C.

(57) ABSTRACT

Cartridges for vaporizer devices are provided. In one exemplary embodiment, the cartridge can include a reservoir housing having a storage chamber and a dispensing chamber, and a vaporization chamber in communication with the dispensing chamber. The storage chamber is configured to hold a first fraction of a vaporizable material and the dispensing chamber is configured to hold a second fraction of the vaporizable material. The dispensing chamber is further configured to selectively dispense at least a first portion of the second fraction of the vaporizable material through at least one dispense opening in response to generation of one or more pressure pulses created within the dispensing chamber. The vaporizable chamber is configured to receive the dispensed vaporizable material from the dispensing chamber for vaporization by a first heating element to form a vaporized material. Vaporizer devices are also provided.

18 Claims, 6 Drawing Sheets

(56) References Cited

U.S. PATENT DOCUMENTS

| | | |
|---|---|---|
| 7,905,230 B2 | 3/2011 | Schuler et al. |
| 7,913,686 B2 | 3/2011 | Hughes et al. |
| 8,079,361 B2 | 12/2011 | Schuler et al. |
| 9,497,994 B2 | 11/2016 | Liu |
| 9,717,276 B2 | 8/2017 | Brammer et al. |
| 9,772,216 B2 | 9/2017 | Poole et al. |
| 10,653,186 B2 * | 5/2020 | Verleur ................ A61M 11/042 |
| 11,006,676 B2 * | 5/2021 | Force .................... A24F 40/485 |
| 2004/0182855 A1 | 9/2004 | Centanni |
| 2005/0016550 A1 | 1/2005 | Katase |
| 2005/0067503 A1 | 3/2005 | Katase |
| 2005/0268909 A1 | 12/2005 | Bonney et al. |
| 2006/0157072 A1 | 7/2006 | Albino et al. |
| 2006/0196505 A1 | 9/2006 | Izuchukwu |
| 2006/0196518 A1 | 9/2006 | Hon |
| 2009/0324206 A1 | 12/2009 | Young et al. |
| 2012/0260927 A1 * | 10/2012 | Liu .......................... A24F 40/46 |
| | | 219/525 |
| 2014/0144429 A1 | 5/2014 | Wensley et al. |
| 2014/0166028 A1 | 6/2014 | Fuisz et al. |
| 2014/0178461 A1 | 6/2014 | Rigas |
| 2014/0190496 A1 | 7/2014 | Wensley et al. |
| 2014/0276536 A1 | 9/2014 | Estes |
| 2014/0360516 A1 | 12/2014 | Liu |
| 2015/0114409 A1 | 4/2015 | Brammer et al. |
| 2015/0157054 A1 | 6/2015 | Liu |
| 2015/0189918 A1 | 7/2015 | Liu |
| 2015/0216237 A1 | 8/2015 | Wensley et al. |
| 2015/0289567 A1 | 10/2015 | Liu |
| 2015/0296885 A1 | 10/2015 | Liu |
| 2015/0296888 A1 | 10/2015 | Liu |
| 2015/0336689 A1 | 11/2015 | Brown et al. |
| 2015/0351455 A1 | 12/2015 | Liu |
| 2016/0073678 A1 | 3/2016 | Fujisawa et al. |
| 2016/0095356 A1 * | 4/2016 | Chan ....................... A24F 40/30 |
| | | 392/390 |
| 2016/0166564 A1 | 6/2016 | Myers et al. |
| 2016/0205999 A1 | 7/2016 | Liu |
| 2016/0227840 A1 | 8/2016 | Xiang |
| 2016/0286865 A1 | 10/2016 | King et al. |
| 2016/0338408 A1 | 11/2016 | Guenther, Jr. et al. |
| 2016/0345625 A1 | 12/2016 | Liu |
| 2016/0360788 A1 * | 12/2016 | Wang ...................... A24F 40/40 |
| 2016/0366935 A1 | 12/2016 | Liu |
| 2017/0017774 A1 | 1/2017 | Skoda |
| 2017/0028178 A1 | 2/2017 | Skoda |
| 2017/0032102 A1 | 2/2017 | Skoda |
| 2017/0042247 A1 | 2/2017 | Xiang |
| 2017/0042248 A1 | 2/2017 | Xiang |
| 2017/0049155 A1 | 2/2017 | Liu |
| 2017/0127727 A1 | 5/2017 | Davidson et al. |
| 2017/0340011 A1 * | 11/2017 | Batista .................... A24F 40/44 |
| 2017/0360093 A1 | 12/2017 | Fernando |
| 2018/0103685 A1 | 4/2018 | Yener |
| 2018/0220707 A1 | 8/2018 | Biel et al. |
| 2020/0005924 A1 * | 1/2020 | Skoda ..................... G16H 20/13 |
| 2020/0128874 A1 | 4/2020 | Atkins et al. |
| 2020/0138114 A1 | 5/2020 | Atkins et al. |
| 2020/0170301 A1 * | 6/2020 | Gallagher .............. A61M 11/02 |

FOREIGN PATENT DOCUMENTS

| | | | |
|---|---|---|---|
| EP | 3062646 A1 | 9/2016 | |
| EP | 3178334 A1 | 6/2017 | |
| EP | 3232834 B1 | 4/2019 | |
| JP | 2001161819 A | 6/2001 | |
| KR | 101324667 B1 | 11/2013 | |
| WO | WO-9501137 A1 | 1/1995 | |
| WO | WO-2012026963 A2 | 3/2012 | |
| WO | WO-2014093127 A2 | 6/2014 | |
| WO | WO-2015066136 A1 | 5/2015 | |
| WO | WO-2015109476 A1 * | 7/2015 | ............. A24F 40/44 |
| WO | WO-2015109618 A1 | 7/2015 | |
| WO | WO-2015157928 A1 | 10/2015 | |
| WO | WO-2016000214 A1 | 1/2016 | |
| WO | WO-2016008096 A1 | 1/2016 | |
| WO | WO-2017063256 A1 | 4/2017 | |
| WO | WO-2017082728 A1 | 5/2017 | |
| WO | WO-2017207415 A1 * | 12/2017 | ............. A24F 40/10 |
| WO | WO-2020187911 A1 * | 9/2020 | ............. A24F 40/10 |

\* cited by examiner

CARTRIDGES FOR VAPORIZER DEVICES

CROSS-REFERENCE TO RELATED APPLICATIONS

This application claims priority to U.S. Provisional Patent Application No. 62/755,886 filed on Nov. 5, 2018, and entitled "Cartridges For Vaporizer Devices," the disclosure of which is incorporated herein by reference in its entirety.

TECHNICAL FIELD

The subject matter described herein relates to vaporizer devices, including vaporizer cartridges.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporizer device.

Vaporizer devices can be controlled by one or more controllers, electronic circuits (for example, sensors, heating elements), and/or the like on the vaporizer device. Vaporizer devices can also wirelessly communicate with an external controller for example, a computing device such as a smartphone).

In some implementations, the vaporizable material can be drawn out of a reservoir and into the vaporization chamber via a wicking element (e.g., a wick). Drawing of the vaporizable material into the vaporization chamber can be at least partially due to capillary action provided by the wicking element as the wicking element pulls the vaporizable material along the wicking element in the direction of the vaporization chamber. However, as vaporizable material is drawn out of the reservoir, the pressure inside the reservoir is reduced, thereby creating a vacuum and acting against the capillary action. This can reduce the effectiveness of the wicking element to draw the vaporizable material into the vaporization chamber, thereby reducing the effectiveness of the vaporizer device to vaporize a desired amount of vaporizable material, such as when a user takes a puff on the vaporizer device. Furthermore, the vacuum created in the reservoir can ultimately result in the inability to draw all of the vaporizable material into the vaporization chamber, thereby wasting vaporizable material. As such, improved vaporizer devices and/or vaporization cartridges that improve upon or overcome these issues are desired.

SUMMARY

Aspects of the current subject matter relate to vaporizer devices and to cartridges for use in a vaporizer device.

In some variations, one or more of the following features may optionally be included in any feasible combination.

In one exemplary embodiment, a cartridge is provided and includes a reservoir housing having a storage chamber and a dispensing chamber, and a vaporization chamber in communication with the dispensing chamber. The storage chamber is configured to hold a first fraction of a vaporizable material and the dispensing chamber is configured to hold a second fraction of the vaporizable material. The dispensing chamber is further configured to selectively dispense at least a first portion of the second fraction of the vaporizable material through at least one dispense opening in response to generation of one or more pressure pulses created within the dispensing chamber. The vaporizable chamber is configured to receive the dispensed vaporizable material from the dispensing chamber for vaporization by a first heating element to form a vaporized material.

The dispensing chamber can have a variety of configurations. For example, in some embodiments, the dispensing chamber can include a second heating element. The second heating element can be configured to selectively vaporize at least a second portion of the second fraction of the vaporizable material in response to activation of the second heating element, in which the vaporization of the second portion of the second fraction of the vaporizable material creates the one or more pressure pulses.

In some embodiments, the at least one dispense opening can be configured to prevent passage of the vaporizable material therethrough when an internal pressure of the reservoir housing is substantially equal to ambient pressure outside of the reservoir housing.

In some embodiments, the storage chamber and the dispensing chamber can be in fluid communication with each other, in which a portion of the first fraction of the vaporizable material can be drawn into the dispensing chamber in response dispensed vaporizable material being expelled from the dispensing chamber.

In some embodiments, the storage chamber and the dispensing chamber can be separated by a reservoir barrier. The reservoir barrier can have at least one orifice extending therethrough. The at least one orifice can be configured to allow a portion of the first fraction of the vaporizable material to be drawn into the dispensing chamber in response to the dispensed vaporizable material being expelled from the dispensing chamber.

In some embodiments, the first heating element can be configured to selectively flash evaporate the dispensed vaporizable material into vaporized material in response to activation of the first heating element.

The vaporization chamber can have a variety of configurations. For example, in some embodiments, the vaporization chamber can define an airflow passageway that extends therethrough. The airflow passageway can be configured to allow the vaporized material to combine with an influx of air to substantially form an aerosol.

In another exemplary embodiment, a cartridge is provided and includes a reservoir housing having a storage chamber and a dispensing chamber, at least one heating element disposed within the dispensing chamber, and a vaporization chamber that is in communication with the dispensing chamber. The storage chamber is configured to hold a first fraction of a vaporizable material and the dispensing chamber is configured to hold a second fraction of the vaporizable material. The at least heating one element is configured to selectively vaporize at least a portion of the second fraction of the vaporizable material into vaporized material. The vaporization chamber is configured to receive the vaporized material from the dispensing chamber. The vaporization chamber is further configured to allow the vaporized material to be withdrawn therefrom.

In some embodiments, the vaporized material can be dispensed from the dispensing chamber and into the vaporization chamber through at least one dispense opening that extends between the dispensing chamber and the vaporization chamber. The at least one dispense opening can be configured to prevent passage of the vaporizable material therethrough when an internal pressure of the reservoir housing is substantially equal to ambient pressure outside of the reservoir housing.

In some embodiments, the storage chamber and the dispensing chamber can be in fluid communication with each other, in which a portion of the first fraction of the vaporizable material can be drawn into the dispensing chamber in response to the vaporized material being dispensed from the dispensing chamber.

In some embodiments, the storage chamber and the dispensing chamber can be separated by a reservoir barrier having at least one orifice extending therethrough. The at least one orifice can be configured to allow a portion of the first fraction of the vaporizable material to be drawn into the dispensing chamber in response to the vaporized material being dispensed from the dispensing chamber.

In another exemplary embodiment, a vaporizer device is provided and includes a vaporizer body and a cartridge that is selectively coupled to and removable from the vaporizer body. The cartridge includes a reservoir housing having a storage chamber and a dispensing chamber, and a vaporization chamber in communication with the dispensing chamber. The storage chamber is configured to hold a first fraction of a vaporizable material and the dispensing chamber is configured to hold a second fraction of the vaporizable material. The dispensing chamber is further configured to selectively dispense at least a first portion of the second fraction of the vaporizable material through at least one dispense opening in response to generation of one or more pressure pulses created within the dispensing chamber. The vaporizable chamber is configured to receive the dispensed vaporizable material from the dispensing chamber for vaporization by a first heating element to form a vaporized material.

The vaporizer body can have variety of configurations. For example, in some embodiments, the vaporizer body can include a power source.

The dispensing chamber can have a variety of configurations. For example, in some embodiments, the dispensing chamber can include a second heating element. The second heating element can be configured to selectively vaporize at least a second portion of the second fraction of the vaporizable material in response to activation of the second heating element, in which the vaporization of the second portion of the second fraction of the vaporizable material can create the one or more pressure pulses.

In some embodiments, the at least one dispense opening can be configured to prevent passage of the vaporizable material therethrough when an internal pressure of the reservoir housing is substantially equal to ambient pressure outside of the reservoir housing.

In some embodiments, the storage chamber and the dispensing chamber are in fluid communication with each other, in which a portion of the first fraction of the vaporizable material can be drawn into the dispensing chamber in response to the dispensed vaporizable material being expelled from the dispensing chamber.

In some embodiments, the storage chamber and the dispensing chamber are separated by a reservoir barrier having at least one orifice extending therethrough. The at least one orifice can be configured to allow a portion of the first fraction of the vaporizable material to be drawn into the dispensing chamber in response to the dispensed vaporizable material being expelled from the dispensing chamber.

In some embodiments, the first heating element can be configured to selectively flash evaporate the dispensed vaporizable material into vaporized material in response to activation of the first heating element.

The vaporization chamber can have a variety of configurations. For example, in some embodiments, the vaporization chamber can define an airflow passageway that extends therethrough. The airflow passageway can be configured to allow the vaporized material to combine with an influx of air to substantially form an aerosol.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a cartridge (for example, a part of the vaporizer device that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material (for example, a carrier solution in which an active and/or inactive ingredient(s) are suspended or held in solution, or a liquid form of the vaporizable material itself). The liquid vaporizable material can be capable of being completely vaporized. Alternatively, at least a portion of the liquid vaporizable material can remain after all of the material suitable for inhalation has been vaporized.

Figure 1A:
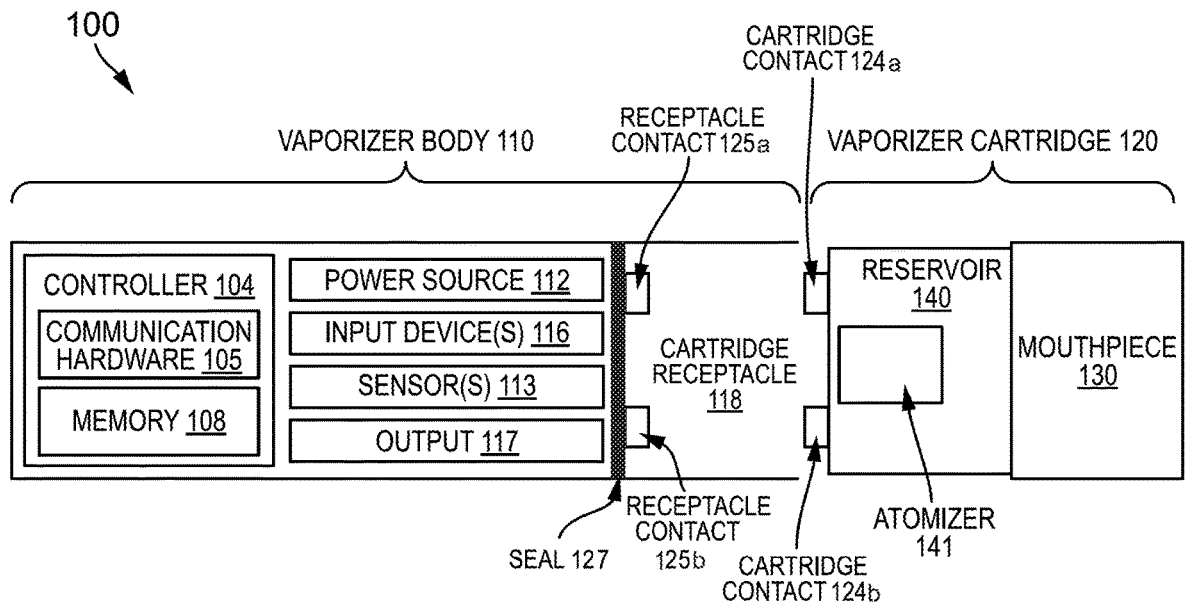
FIG. 1A is a block diagram of a vaporizer device.

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer device and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wicking element for vaporization by the heating element, and air can return to the reservoir 140 through the wicking element to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer device, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

For example, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
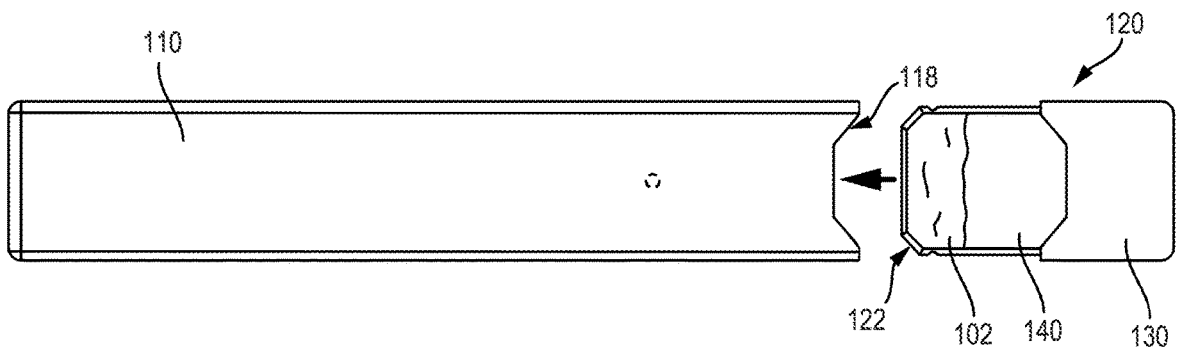
FIG. 1B is a top view of an embodiment of a vaporizer device, showing a vaporizer cartridge separated from a vaporizer device body.
Figure 1C:
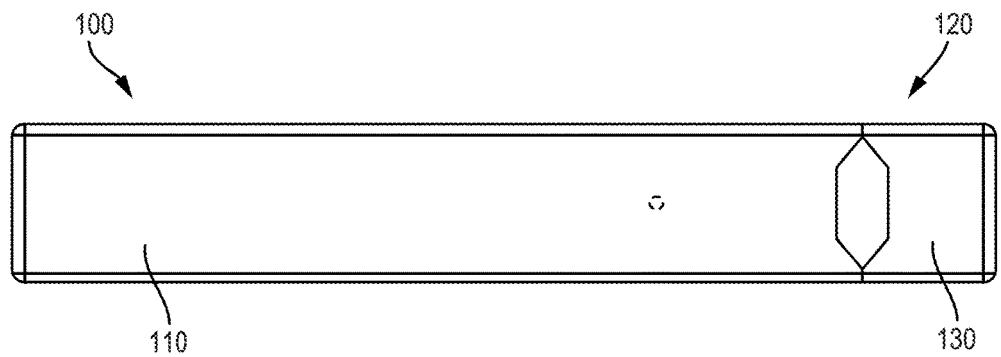
FIG. 1C is a top view of the vaporizer device of FIG. 1B, showing the vaporizer cartridge coupled to the vaporizer device body.
Figure 1D:
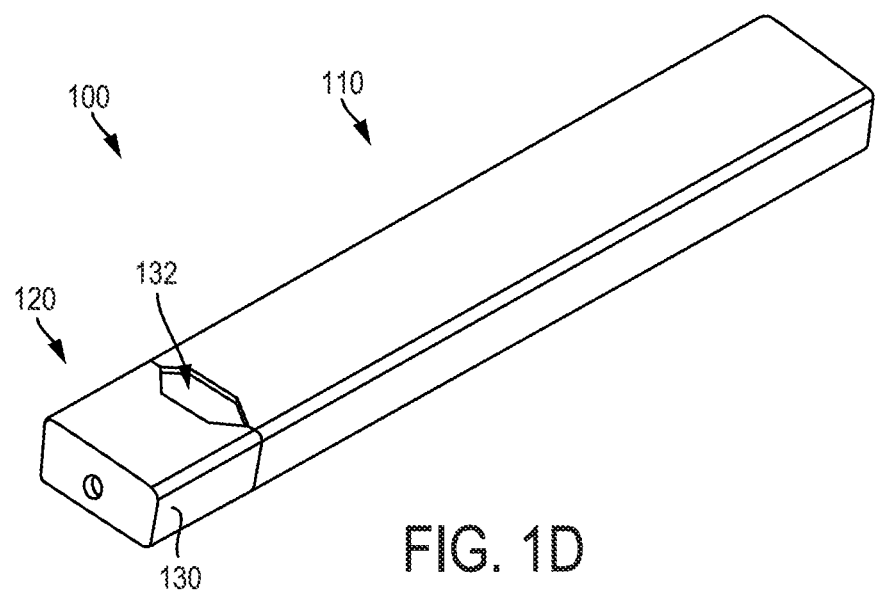
FIG. 1D is a perspective view of the vaporizer device of FIG. 1C.

FIGS. 1B-1D illustrate an embodiment of the vaporizer body 110 having a cartridge receptacle 118 into which the vaporizer cartridge 120 can be releasably inserted. FIGS. 1B and 1C show top views of the vaporizer device 100 illustrating the vaporizer cartridge 120 being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 can be configured such that the window 132 remains visible when insertably received by the vaporizer cartridge receptacle 118 of the vaporizer body 110. For example, in one exemplary configuration, the window 132 can be disposed between a bottom edge of the mouthpiece 130 and a top edge of the vaporizer body 110 when the vaporizer cartridge 120 is coupled with the cartridge receptacle 118.

Figure 1E:
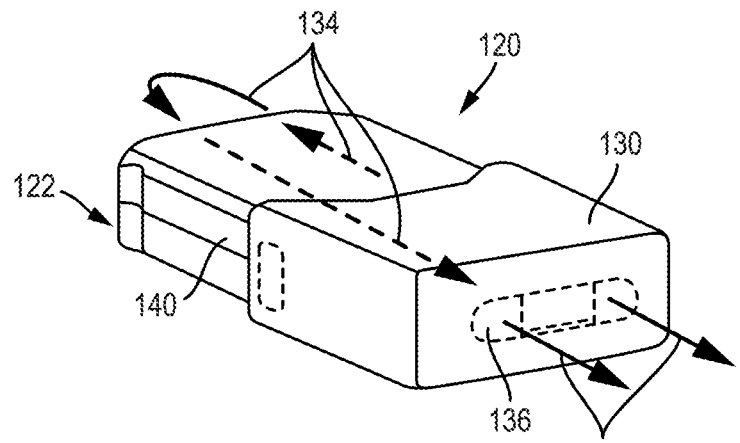
FIG. 1E is a perspective view of the vaporizer cartridge of FIG. 1B.

FIG. 1E illustrates an example airflow path 134 created during a puff by a user on the vaporizer device 100. The airflow path 134 can direct air to a vaporization chamber 150 (see FIG. 1F) contained in a wick housing where the air is combined with inhalable aerosol for delivery to a user via a mouthpiece 130, which can also be part of the vaporizer cartridge 120. For example, when a user puffs on the vaporizer device 100 device 100, air can pass between an outer surface of the vaporizer cartridge 120 (for example, window 132 shown in FIG. 1D) and an inner surface of the cartridge receptacle 118 on the vaporizer body 110. Air can then be drawn into the insertable end 122 of the vaporizer cartridge 120, through the vaporization chamber 150 that includes or contains the heating element and wicking element, and out through an outlet 136 of the mouthpiece 130 for delivery of the inhalable aerosol to a user.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite of the end including the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128 shown in FIG. 1F) and through one or more outlets (such as outlet 136) formed in the mouthpiece 130. The mouthpiece 130 can be a separable component of the vaporizer cartridge 120 or can be integrally formed with other component(s) of the vaporizer cartridge 120 (for example, formed as a unitary structure with the reservoir 140 and/or the like).

Figure 1F:
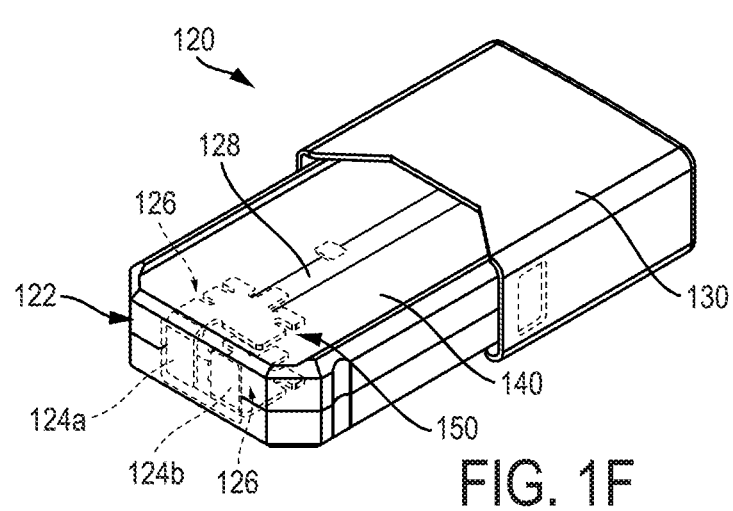
FIG. 1F is another perspective view of the vaporizer cartridge of FIG. 1E.

FIG. 1F shows additional features that can be included in the vaporizer cartridge 120 consistent with implementations of the current subject matter. For example, the vaporizer cartridge 120 can include a plurality of cartridge contacts (such as cartridge contacts 124a, 124b) disposed on the insertable end 122. The cartridge contacts 124a, 124b can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows the cannula 128 within the vaporizer cartridge 120 that defines part of the airflow path 134 between the heating chamber formed between the conductive structure 126 and the mouthpiece 130.

As mentioned above, existing vaporizer cartridges can include a wicking element that is generally configured to withdraw a vaporizable material from a reservoir housing such that the vaporizable material may be subsequently vaporized (e.g., by exposing the withdrawn vaporizable material to heat provided by a heating element). As used herein, "reservoir housing" is used synonymously with "reservoir."

The withdrawal of the vaporizable material from the reservoir housing can be due, at least in part, to capillary action provided by the wicking element, which pulls the vaporizable material along the wicking element in the direction towards a vaporization chamber. As a result, the vaporizable material is fed into the wicking element by capillary action. The feed rate, however, can be a function of, at least in part, on the amount of vaporizable material contained within the reservoir housing. Thus, as more and more vaporizable material is being withdrawn out of the reservoir housing during use, less vaporizable material is present within the reservoir housing. This can reduce the feed rate, and ultimately, the effectiveness of the wicking element to withdraw the vaporizable material into the vaporization chamber. Under such circumstances, the effectiveness of the vaporizer device to vaporize a desired amount of vaporizable material, such as when a user takes a puff on the vaporizer cartridge, can be reduced.

Various features and devices are described below that improve upon or overcome the aforementioned issues. For example, various features are described herein that replace the wicking element with a pumping mechanism that is configured to pump the vaporizable material from the reservoir housing and into a vaporization chamber. The pumping mechanism can achieve a feed rate that is substantially independent of the amount of vaporizable material contained within the reservoir housing. Implementing a pumping mechanism, as opposed to using a wicking element, may provide advantages and improvements relative to existing approaches, while also introducing additional benefits, as described herein.

The vaporizer cartridges described herein allow a desired amount of vaporizable material to be pumped out of a reservoir housing at a rate that is substantially independent of the amount of vaporizable material within the reservoir housing. Further, the pumping of the vaporizable material can be substantially achieved without the use of moving parts. The vaporizer cartridges generally include a reservoir housing having a storage chamber configured to hold a first fraction of a vaporizable material and a dispensing chamber configured to hold a second fraction of the vaporizable material. As discussed in more detail below, the dispensing chamber is also configured to selectively dispense at least a first portion of the second fraction of the vaporizable material (or alternatively, a portion of vaporized material) in response to the creation of one or more pressure pulses within the dispensing chamber. These one or more pressure pulses are each created by the formation of a respective pocket or bubble of vaporized material within the dispensing chamber. Each pocket or bubble of vaporized material can force the first portion of the second fraction of vaporizable material through at least one dispense opening of the dispensing chamber. Alternatively, each pocket or bubble of vaporized material can be forced through the at least one dispense opening of the dispensing chamber by the pressure created during each respective pressure pulse.

Figure 2A:
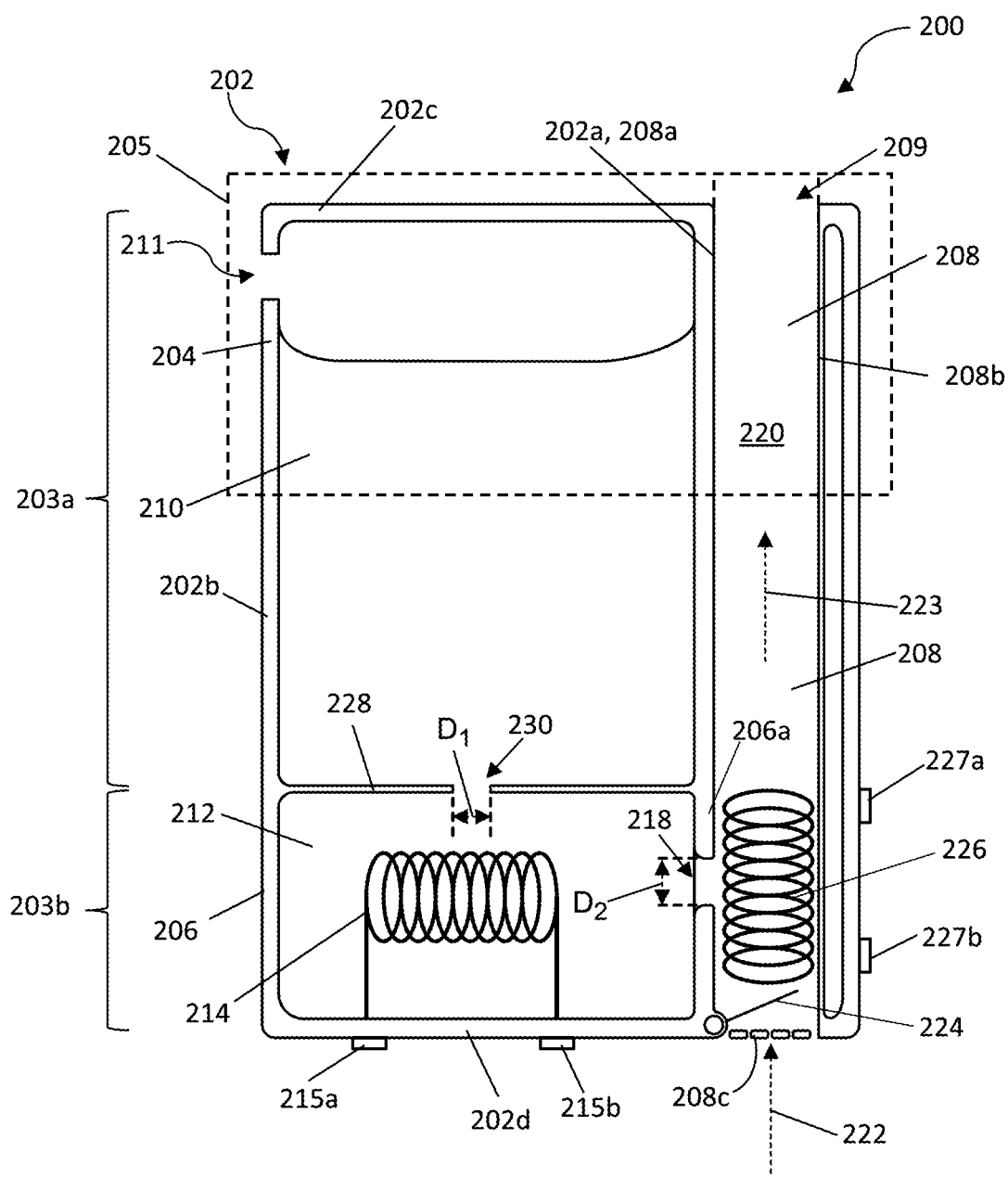
FIG. 2A illustrates a schematic of another embodiment of a vaporizer cartridge, showing the vaporizer cartridge prior to a pressure pulse.
Figure 2B:
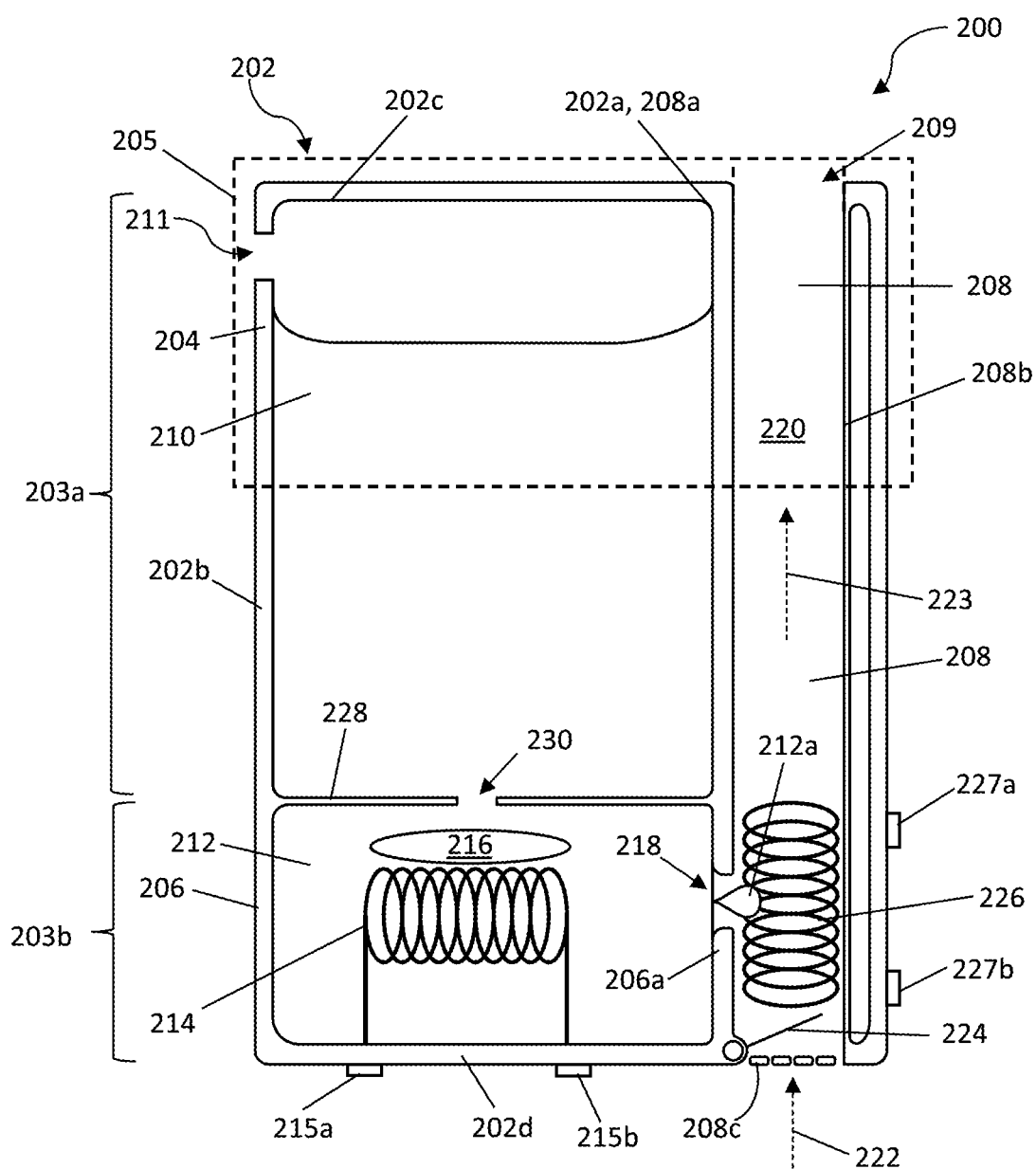
FIG. 2B illustrates the vaporizer cartridge of FIG. 2A during a pressure pulse.

FIGS. 2A-2B illustrate an exemplary vaporizer cartridge 200 that can be selectively coupled to and removable from a vaporizer body, such as vaporizer body 110 shown in FIGS. 1A-1D). vaporizer cartridge. More specifically, the vaporizer cartridge 200 includes a reservoir housing 202 having a dispensing chamber 206 that is configured to dispense a portion of vaporizable material from the reservoir housing 202 into a vaporization chamber 208 using a pumping mechanism that is actuated in response to, for example, a user puffing on a mouthpiece 205 coupled with the vaporizer cartridge 200. While a mouthpiece 205 is shown in FIGS. 2A-2B, a person skilled in the art will appreciate that in other embodiments, the mouthpiece 205 can be omitted and the user can directly puff on the cartridge at an outlet (such as outlet 209 of vaporization chamber 208). For purposes of simplicity, certain components of the vaporizer cartridge 200 are not illustrated.

As shown, the reservoir housing 202 has an inner volume defined by at least a first pair of opposing reservoir walls 202a, 202b and a second pair of opposing reservoir walls 202c, 202d. The reservoir housing 202 includes a storage chamber 204 that is configured to hold a first fraction of a vaporizable material 210 and the dispensing chamber 206 that is configured to hold a second fraction of the vaporizable material 212. The first fraction of vaporizable material 210 and the second fraction of the vaporizable material 212 are collectively referred to herein as "vaporizable material." While the respective inner volumes of the storage chamber 204 and the dispensing chamber 206 can vary, the combined inner volumes of the storage chamber 204 and the dispensing chamber 206, as shown in FIGS. 2A-2B, is equal to the inner volume of the reservoir housing 202. This configuration may be desirable to maximize the amount of vaporizable material that can be disposed into the reservoir housing 202.

While the shape and size of the storage chamber 204 and the dispensing chamber 206 can vary, each chamber, as shown in FIGS. 2A-2B, is substantially rectangular in shape with the storage chamber 204 being greater in size relative to the dispensing chamber 206. It may be desirable to have a greater inner volume within the storage chamber 204 compared to dispensing chamber 206 so as to maximize the amount of vaporizable material that can be stored within the reservoir housing 202 without substantially inhibiting the pumping mechanism within the dispensing chamber 206, as discussed in more detail below. In other embodiments, the storage chamber 204 can have a different shape and/or be smaller in size compared to the dispensing chamber 206.

While the storage chamber 204 and the dispensing chamber 206 can be positioned relative to each other and within the reservoir housing 202 in a variety of locations. FIGS. 2A-2B depicts one example configuration in which the storage chamber 204 is positioned within a top portion 203a of the reservoir housing 202 and the dispensing chamber 206 is positioned within a bottom portion 203b of the reservoir housing 202. It may be desirable to position the dispensing chamber 206 below the storage chamber 204 to enhance the flow of the first fraction of the vaporizable material 210 into the dispensing chamber 206. Further, such a position may also be desirable because it can inhibit a vacuum created within the storage chamber 204 from adversely affecting the dispensing of vaporizable material (or vaporized material) from the dispensing chamber 206.

In general, as discussed above, the dispensing chamber 206 is configured to dispense a portion of the second fraction of the vaporizable material 212, such as second portion 212a shown in FIG. 2B, into the vaporization chamber 208 using a pumping mechanism. While the pumping mechanism can have a variety of configuration, the pumping mechanism, as shown in FIGS. 2A-2B, includes a first heating element 214 disposed within the dispensing chamber 206. This first heating element 214 is configured to at least partially vaporize a portion of the second fraction of the vaporizable material 212 that is in close proximity to, and/or in contact with, the first heating element 214 at the time of activation of the first heating element 214. Once the portion of the second fraction of the vaporizable material 212 is at least partially vaporized, the first heating element 214 can be deactivated, or alternatively, the temperature of the first heating element 214 can be reduced to prevent further vaporization until desired.

The first heating element 214 can be or include one or more of a conductive heater, a radiative heater, and a convective heater. As discussed above, one type of heating element is a resistive heating element, such as a resistive coil, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. As shown in FIGS. 2A-2B, the first heating element 214 is in the form of a resistive coil.

In some embodiments, the vaporizer cartridge 200 includes two or more cartridge contacts such as, for example, a first cartridge contact 215a and a second cartridge contact 215b. The two or more cartridge contacts can be configured to couple, for example, with the receptacle contacts 125a and 125b in order to form one or more electrical connections with the vaporizer body 110. The circuit completed by these electrical connections can allow delivery of electrical current to the first heating element 214. The circuit can also serve additional functions such as, for example, measuring a resistance of the first heating element 214 for use in determining and/or controlling a temperature of the first heating element 214 based on a thermal coefficient of resistivity of the first heating element 214.

The first heating element 214 can be positioned in a variety of locations within the dispensing chamber 206. For example, as shown in FIGS. 2A-2B, the first heating element 214 is substantially centered within the dispensing chamber 206. It may be desirable to align at least a portion of the first heating element 214 with a passageway, such as dispense opening 218, that is configured to allow a portion of the second fraction of vaporizable material 212 to be selectively dispensed from the dispensing chamber 206. Alternatively, or in addition, it may be desirable to align at least a portion of the first heating element 214 with a passageway, such as orifice 230, that is configured to allow a portion of the first fraction of the vaporizable material 210 to selectively flow into the dispensing chamber 206.

As discussed above, the first heating element 214 can have a variety of configurations and can be activated/reactivated in a variety of ways. Once the first heating element 214 is activated, for example, concurrent with and/or after a user puffs on the mouthpiece 205, heat is expelled therefrom. As the heat reaches a temperature that is substantially equal to the boiling point of the vaporizable material disposed within the reservoir housing 202, a portion of the second fraction of the vaporizable material 212 that is in close proximity to, and/or in contact with, the first heating element 214 is vaporized, as shown in FIG. 2B. As a result, a pocket or bubble of the vaporized material 216 is formed, as shown in FIG. 2B, which generates a pressure pulse within the dispensing chamber 206. That is, the pressure pulse is generated by the first heating element 214 momentarily vaporizing a portion of the second fraction of the vaporizable material 212. This pressure pulse forces a second portion 212a of the second fraction of the vaporizable material 212 to be expelled out of the dispensing chamber 206, as shown in FIG. 2B. Thus, this pressure pulse generally functions as a pumping mechanism that pumps vaporizable material from the reservoir housing 202 and into the vaporization chamber 208 in response to at least a partial, temporary vaporization of a portion of the second fraction of the vaporizable material 212. As such, this pumping mechanism relies on the pressure pulse, rather than the amount of vaporizable material contained within the reservoir housing 202. Further, this pumping mechanism is configured such that substantially no moving parts are required to effect the resulting pumping of the vaporizable material (or vaporized material) from the dispensing chamber 206.

While the size of the pocket or bubble of the vaporized material 216 can vary, the first heating element 214 is configured to produce a pocket or bubble having a size that inhibits the pocket or bubble from coming into contact with, and thus released through, at least the dispense opening 218. In some embodiments, the size of the pocket or bubble also prevents the pocket or bubble from coming into contact with, and thus flow through, orifice 230. Thus, the first heating element 214 is configured to vaporize an amount of vaporizable material that forms a pocket or bubble that stays, and collapses, within the dispensing chamber 206.

Further, during use, the first heating element 214 can create two or more sequential pockets or bubbles, thus two or more sequential pressure pulses, during activation (e.g., while a user is drawing on the mouthpiece 205). Each of these pockets or bubbles can separately expel a respective second portions 212a of the second fraction of the vaporizable material 212 out of the dispensing chamber 206. Thus, the first heating element 214 can be configured to create one or more sequential pockets or bubbles of vaporized material during activation.

The dispensing chamber 206 can include a variety of dispensing configurations and features that allow for expulsion of the second portion 212a of the second fraction of the vaporizable material 212 in response to the pressure pulse. In some embodiments, the dispensing chamber 206 can include one or more dispensing openings that extend between the dispensing chamber 206 and the vaporization chamber 208. In the example shown in FIGS. 2A-2B, the dispensing chamber 206 includes one dispense opening 218 that extends through a wall 206a of the dispensing chamber 206, and thus between the dispensing chamber 206 and the vaporization chamber 208. As illustrated, the wall 206a of the dispensing chamber 206 is part of one of the sidewalls (such as sidewall 208a) of the vaporization chamber 208. The dispense opening 218 is configured to allow the second portion 212a of the second fraction of the vaporizable material 212 to pass therethrough, and thus from the dispensing chamber 206 and into the vaporization chamber 208, in response to the pressure pulse.

The dispense opening 218 can have a variety of configurations. For example, as shown in FIGS. 2A-2B, the dispense opening 218 forms a passageway that extends between the dispensing chamber 206 and an airflow passageway 220 defined by the vaporization chamber 208. In this way, in response to the generation of the pressure pulse, the second portion 212a of the second fraction of the vaporizable material 212 can be expelled from the dispensing chamber 206 through this passageway and into the airflow passageway 220 for subsequent vaporization by another heater, such as second heating element 226 shown in FIGS. 2A-2B. The dispense opening 218 can also have a diameter that is sized to substantially prevent the passage of the vaporizable material (e.g., a portion of the second fraction of the vaporizable material 212) therethrough, when an internal pressure of the reservoir housing 202 is substantially equal to ambient pressure outside of the reservoir housing 202. That is, the dispense opening 218 can include a diameter that is sized such that a surface tension of the second fraction of the vaporizable material 212 is created to thereby substantially prevent any vaporizable material from passing through, and thus out of the dispensing chamber 206, when the pressure is equalized across the dispense opening 218.

While the vaporization chamber 208 can have a variety of configurations, the vaporization chamber 208, as shown in FIGS. 2A-2B, is defined by at least two opposing sidewalls 208a, 208b, one of which is the sidewall 202a of the reservoir housing 202, and a bottom wall 208c extending therebetween. As such, in this illustrated embodiment, the sidewalls 208a, 208b of the vaporization chamber 208 extends substantially parallel with the sidewalls 202a, 202b of the reservoir housing 202. As shown, the vaporization chamber 208 defines the airflow passageway 220 that extends therethrough. The airflow passageway 220 is configured to direct air, illustrated as dash-lined-lined arrow 222, through the vaporization chamber 208 so that the air 222 will mix with the vaporized material to form an aerosol, illustrated as dash-lined arrow 223. The airflow passageway 220 further directs the aerosol 223 through the outlet 209 of the vaporization chamber 208, and thus the mouthpiece 205, for inhalation by a user.

In some embodiments, at least one wall of the vaporization chamber 208, such as sidewall 208a which is also sidewall 202a of the reservoir housing 202, can be formed of, or coated with, a hydrophobic material so as to prevent any condensation from accumulating within the vaporization chamber 208. As such, any water that may be present in the aerosol 223 and in the air 222 can be carried through and out of the vaporization chamber 208 as the user puffs on the mouthpiece 205.

The air 222 enters the vaporization chamber 208 through the bottom wall 208c as a user puffs on the mouthpiece 205. As such, the bottom wall 208c is configured to allow the air 222 to readily pass therethrough and into the vaporization chamber 208. While the bottom wall 208c can have a variety of configurations, the bottom wall 208c is perforated, as shown in FIGS. 2A-2B. The perforations can be of any suitable size that allows air to pass through the bottom wall 208c. In certain embodiments, the size of the perforations can substantially prevent any vaporizable material dispensed from the dispensing chamber 206 or aerosol 223 to pass through the bottom wall 208c, and therefore inhibit undesirable leakage into other portions of the device. The bottom wall 208c can include any suitable number of perforations, and therefore the number of perforations is not limited by what is illustrated in the FIGS. 2A-2B. Alternatively or in addition, the bottom wall 208c can be formed of an air permeable material. Thus, the bottom wall 208c functions as an air inlet for the vaporization chamber 208.

Further, as shown in FIGS. 2A-2B, the vaporization chamber 208 can include a valve 224 that is configured to allow air 222 to enter the vaporization chamber 208 through the bottom wall 208c. As such, the valve 224 can function as a one-way valve. The valve 224 can be configured to prevent any vaporizable material that may be expelled into the vaporization chamber 208 but not vaporized from leaking through the bottom wall 208c of vaporization chamber 208. Alternatively, or in addition, the valve 224 can be configured to prevent air 222 and/or aerosol within the vaporization chamber 208 from passing through the bottom wall 208c. The valve 224 can be mechanically and/or electronically controlled. Various configurations of the valve 224 are contemplated herein.

Alternatively, or in addition, the bottom wall 208c can also be configured to prevent air 222 and/or aerosol within the vaporization chamber 208 from passing therethrough. That is, the bottom wall 208c can be configured as a one-way valve, and therefore only allow air 222 to pass through and into the vaporization chamber 208. In some embodiments, any of the remaining walls of the vaporization chamber 208 can be perforated and/or formed of an air permeable material to allow air to pass into (or out of) the vaporization chamber 208 as desired.

As further shown in FIGS. 2A-2B, a second heating element 226 is disposed within the vaporization chamber 208. The second heating element 226 is configured to selectively flash evaporate the vaporizable material that is dispensed from the dispensing chamber 206 in response to the pressure pulse. That is, when activated, for example, concurrent with and/or after a user puffs on the mouthpiece 205, the second heating element 226 causes substantially instantaneous vaporization of the second portion 212a of the second fraction of the vaporizable material 212 that is expelled into the vaporization chamber 208. Thus, when activated, the second heating element 226 achieves a steady-state temperature that is at least substantially equal to the vaporization temperature of the vaporizable material disposed within the reservoir housing 202. As a result, when the dispensed portion of the vaporizable material (e.g., the second portion 212a of the second fraction of the vaporizable material 212) is brought into close proximity of, or in contact with, a surface of the second heating element 226, the dispensed portion is instantaneously vaporized into vaporized material. This vaporized material can then combine with the air 222 passing through the airflow passageway 220 of the vaporization chamber 208. As a result, the vaporized material is condensed into an aerosol 223 that is subsequently inhaled by a user through the outlet 209 of the vaporization chamber, and thus the mouthpiece 205.

The second heating element 226 can be or include one or more of a conductive heater, a radiative heater, and a convective heater. As discussed above, one type of heating element is a resistive heating element, such as a resistive coil, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. As shown in FIGS. 2A-2B, the second heating element 226 is in the form of a resistive coil. The second heating element 226 can have a variety of shapes and sizes. For example, the second heating element 226 can have a greater size compared to that of the first heating element 214.

In some embodiments, the vaporizer cartridge 200 includes two or more cartridge contacts such as, for example, a first cartridge contact 227a and a second cartridge contact 227b. The two or more cartridge contacts can be configured to couple, for example, with the receptacle contacts 125a and 125b in order to form one or more electrical connections with the vaporizer body 110. The circuit completed by these electrical connections can allow delivery of electrical current to the second heating element 226. The circuit can also serve additional functions such as, for example, measuring a resistance of the second heating element 226 for use in determining and/or controlling a temperature of the second heating element 226 based on a thermal coefficient of resistivity of the second heating element 226.

While the second heating element 226 can be disposed within the vaporization chamber 208 at a variety of locations, the second heating element 226, as shown in FIGS. 2A-2B, is positioned proximate to the bottom wall 208c of the vaporization chamber 208. Further, as shown in FIGS. 2A-2B, the second heating element 226 is also positioned adjacent to the dispense opening 218. This illustrated position may be desired to help maximize the amount of vaporizable material that is brought into close proximity of, or in contact with, the second heating element 226, thereby enhancing the effectiveness of the vaporization thereof. The second heating element 226 being positioned within a close proximity of the dispense opening 218 can also allow for a faster and more direct flow of the dispensed vaporizable material toward the second heating element 226 for vaporization.

Further, as shown in FIGS. 2A-2B, the storage chamber 204 and dispensing chamber 206 are separated by a reservoir barrier 228 that is configured to allow the storage chamber 204 to be in fluid communication with the dispensing chamber 206. While the reservoir barrier 228 can have a variety of configurations, the reservoir barrier 228 can include one or more orifices that extend therethrough. In the example shown in FIGS. 2A-2B, the reservoir barrier 228 includes an orifice 230 configured to allow a portion of the first fraction of the vaporizable material 210 to flow into the dispensing chamber 206 (e.g., as the pocket or bubble 216 collapses due to condensation, thereby creating a vacuum within the dispensing chamber 206), thereby creating a pressure equilibrium across the dispense opening 218. In other embodiments, at least a portion of the reservoir barrier 228 can be formed of a permeable material.

Figure 3:
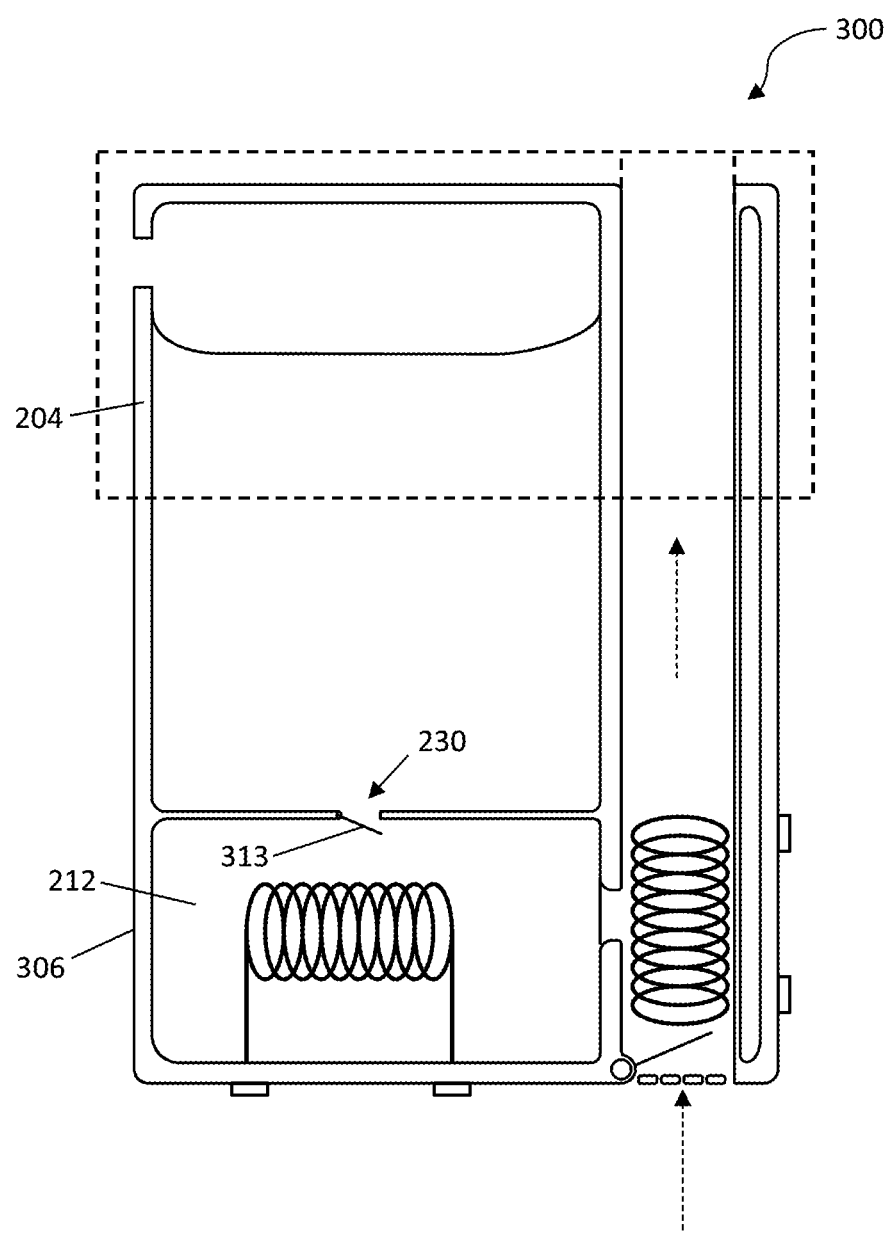
FIG. 3 illustrates another embodiment of a vaporizer cartridge.

In this illustrated embodiment, the dispense opening 218 and the orifice 230 are each configured such that there is low resistance flow through the dispense opening 218 as compared to the orifice 230. As shown, the size ($D_1$) of the orifice 230 is less than the size ($D_2$) of the dispense opening 218. In other embodiments, a one-way valve can be used. For example, as shown in FIG. 3, a vaporizer cartridge 300 includes a dispensing chamber 306 that includes a one-way valve 313 that is configured to prevent backflow of the second fraction of vaporizable material 212 through orifice 230 into the storage chamber 204 upon the collapse of each pocket or bubble formed.

Referring back to FIGS. 2A-2B, during use, once the second portion 212a is dispensed from the dispensing chamber 206, the pocket or bubble within the dispensing chamber 206 collapses. As a result, a vacuum is created within the dispensing chamber 206. This vacuum draws a portion of the first fraction of the vaporizable material 210 from the storage chamber 206 into the dispensing chamber 206 through the orifice 230 to replenish the dispensed volume of the second fraction of the vaporizable material 212. As a result, the volume of the first fraction of the vaporizable material 210 decreases after each second portion 212a is dispensed from the dispensing chamber 206.

Further, during use, as the volume of the first fraction of vaporizable material 210 decreases, e.g., as portions of the first fraction of the vaporizable material 210 flow into the dispensing chamber 206 via orifice 230, negative pressure can be created in the storage chamber 204. This negative pressure can prevent further portions of the first fraction of vaporizable material 210 from flowing into the dispensing chamber 206, and thus additional portions of the second faction of vaporizable material 212 from being dispensed from the dispensing chamber 206 and into the vaporization chamber 208. To eliminate or reduce this negative pressure, the pressure within storage chamber 204 can be increased as portions of the second fraction of vaporizable material 212 are each dispensed. For example, in some embodiments, the storage chamber 204 can include one or more vents, e.g., vent 211, that are configured to selectively allow the passage of air into the storage chamber 206 from the environment to thereby substantially maintain an inner pressure (e.g., an inner pressure that is substantially equal to ambient pressure) of the storage chamber 204. That is, vent 211 allows ambient air to enter into the storage chamber 204, thereby eliminating the creation of a counter vacuum that acts against the vacuum created within the dispensing chamber 206 when the pocket or bubble collapses. Thus, as each pocket or bubble collapses within the dispensing chamber 206, a portion of the first fraction of the vaporizable material 210 can flow through orifice 230 and into the dispensing chamber 206.

While the foregoing embodiment of the vaporizer cartridge has been discussed in the context of at least two heating elements, alternative embodiments of the vaporizer cartridge may employ a single heating element or additional heating elements.

Figure 4:
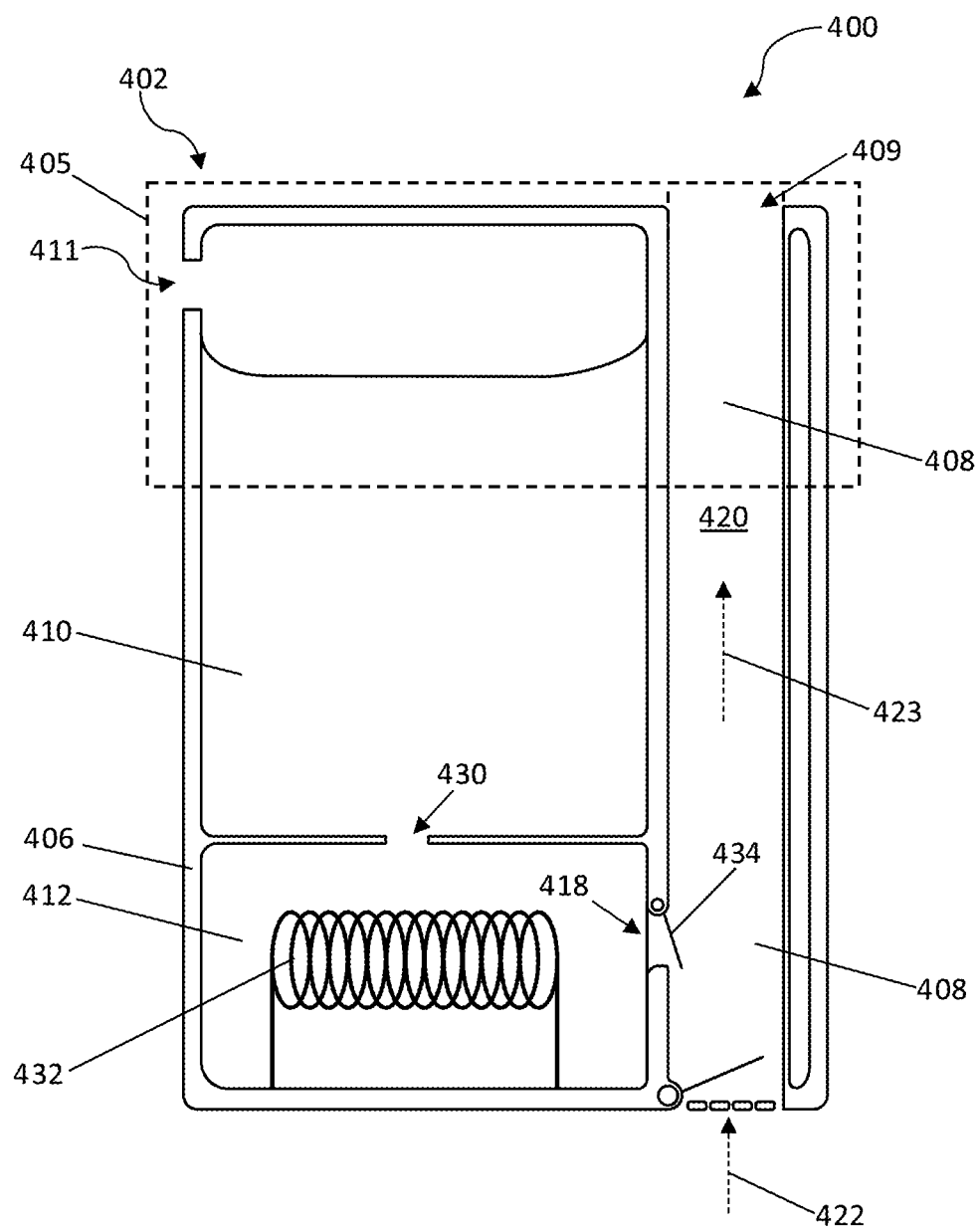
FIG. 4 illustrates another embodiment of a vaporizer cartridge.

FIG. 4 illustrates another exemplary vaporizer cartridge 400 that can be selectively coupled to and removable from a vaporizer body, such as vaporizer body 110 shown in FIGS. 1A-1D. Aside from the differences described below, the vaporizer cartridge 400 can be similar to vaporizer cartridge 200 (FIGS. 2A-2B) and therefore similar features are not described in detail herein.

In this illustrated example, the vaporizer cartridge 400 includes only a single heating element, i.e., heating element 432. As shown, the heating element 432 is disposed within the dispensing chamber 406. The heating element 432 is configured to selectively flash evaporate a portion of the vaporizable material 412 to produce a pocket or bubble having a sufficient volume of vaporized material such that the pocket or bubble comes into contact with, and therefore can be expelled directly through, the dispense opening 418 of the dispensing chamber 406, and into the vaporization chamber 408. That is, when activated, the heating element 432 allows for substantially instantaneous vaporization of the portion of the vaporizable material that is in close proximity of, or in contact with, a surface of the heating element 432. Thus, when activated, the heating element 432 has a steady-state temperature that is greater than the vaporization temperature of the vaporizable material disposed within the reservoir housing 402. As a result, the production of vaporized material occurs only within the dispensing chamber 406.

The vaporized material can then be expelled into the vaporization chamber 408, where the vaporized material combines with the air 422 passing through the airflow passageway 420. As a result, the vaporized material is condensed into an aerosol 423 that is subsequently inhaled by a user through the outlet 409, and thus mouthpiece 405.

Further, as shown in FIG. 4, the vaporizer cartridge 400 includes a one-way valve 434 that is configured to prevent backflow of air 422 and aerosol 423 into the dispensing chamber 406 once the vaporized material is expelled therefrom. As a result, once the vaporized material is dispensed into the vaporization chamber, the one-way valve closes, thereby allowing a vacuum to be created within the dispensing chamber 406. This vacuum draws a portion of the first fraction of vaporizable material 410 through orifice 430 and replenishes the dispensing chamber 406. As such, in this illustrated embodiment, the dispensing chamber 406 is configured to hold one dose of vaporizable material for each puff on the mouthpiece 405.

Various other configurations of a vaporizer cartridge using a single heating element is also contemplated herein.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A cartridge for a vaporizer device, the cartridge comprising:
   a reservoir housing having a storage chamber configured to hold a first fraction of a vaporizable material and a dispensing chamber configured to hold a second fraction of the vaporizable material, the dispensing chamber being further configured to selectively dispense at least a portion of the second fraction of the vaporizable material through at least one dispense opening in response to generation of one or more pressure pulses created within the dispensing chamber; and
   a vaporization chamber in fluid communication with the dispensing chamber, the vaporization chamber being configured to receive the dispensed vaporizable material from the dispensing chamber for vaporization by a first heating element to form a vaporized material,
   wherein the dispensing chamber includes a second heating element that is configured to selectively vaporize at least a second portion of the second fraction of the vaporizable material in response to activation of the second heating element, and wherein the vaporization of the second portion of the second fraction of the vaporizable material creates the one or more pressure pulses.

2. The cartridge of claim 1, wherein the at least one dispense opening is configured to prevent passage of the vaporizable material therethrough when an internal pressure of the reservoir housing is substantially equal to ambient pressure outside of the reservoir housing.

3. The cartridge of claim 1, wherein the storage chamber and the dispensing chamber are in fluid communication with each other, and wherein a portion of the first fraction of the vaporizable material is drawn into the dispensing chamber in response to the dispensed vaporizable material being expelled from the dispensing chamber.

4. The cartridge of claim 1, wherein the storage chamber and the dispensing chamber are separated by a reservoir barrier having at least one orifice extending therethrough, and wherein the at least one orifice is configured to allow a portion of the first fraction of the vaporizable material to be drawn into the dispensing chamber in response to the dispensed vaporizable material being expelled from the dispensing chamber.

5. The cartridge of claim 1, wherein the first heating element is configured to selectively flash evaporate the dispensed vaporizable material into vaporized material in response to activation of the first heating element.

6. The cartridge of claim 1, wherein the vaporization chamber defines an airflow passageway that extends therethrough, and wherein the airflow passageway is configured to allow the vaporized material to combine with an influx of air to substantially form an aerosol.

7. A cartridge for a vaporizer device, the cartridge comprising:
   a reservoir housing having a storage chamber configured to hold a first fraction of a vaporizable material and a dispensing chamber configured to hold a second fraction of the vaporizable material;
   at least one heating element disposed within the dispensing chamber, the at least one heating element being configured to selectively vaporize at least a portion of the second fraction of the vaporizable material into vaporized material; and
   a vaporization chamber in communication with the dispensing chamber, the vaporization chamber being configured to receive the vaporized material from the dispensing chamber and configured to allow the vaporized material to be withdrawn therefrom, wherein the vaporization chamber includes at least another heating element disposed therein.

8. The cartridge of claim 7, wherein the vaporized material is dispensed from the dispensing chamber and into the vaporization chamber through at least one dispense opening that extends between the dispensing chamber and the vaporization chamber.

9. The cartridge of claim 8, wherein the at least one dispense opening is configured to prevent passage of the vaporizable material therethrough when an internal pressure of the reservoir housing is substantially equal to ambient pressure outside of the reservoir housing.

10. The cartridge of claim 7, wherein the storage chamber and the dispensing chamber are in fluid communication with each other, and wherein a portion of the first fraction of the vaporizable material is drawn into the dispensing chamber in response to the vaporized material being dispensed from the dispensing chamber.

11. The cartridge of claim 7, wherein the storage chamber and the dispensing chamber are separated by a reservoir barrier having at least one orifice extending therethrough, and wherein the at least orifice is configured to allow a portion of the first fraction of the vaporizable material to be drawn into the dispensing chamber in response to the vaporized material being dispensed from the dispensing chamber.

12. A vaporizer device, comprising:
a vaporizer body; and
a cartridge that is selectively coupled to and removable from the vaporizer body, the cartridge including:
a reservoir housing having a storage chamber configured to hold a first fraction of a vaporizable material and a dispensing chamber configured to hold a second fraction of the vaporizable material, the dispensing chamber being further configured to selectively dispense at least a portion of the second fraction of the vaporizable material through at least one dispense opening in response to generation of one or more pressure pulses created within the dispensing chamber, and
a vaporization chamber in fluid communication with the dispensing chamber, the vaporization chamber being configured to receive the dispensed vaporizable material from the dispensing chamber for vaporization by a first heating element to form a vaporized material,
wherein the dispensing chamber includes a second heating element that is configured to selectively vaporize at least a second portion of the second fraction of the vaporizable material in response to activation of the second heating element, and wherein the vaporization of the second portion of the second fraction of the vaporizable material creates the one or more pressure pulses.

13. The device of claim 12, wherein the vaporizer body includes a power source.

14. The device of claim 12, wherein the at least one dispense opening is configured to prevent passage of the vaporizable material therethrough when an internal pressure of the reservoir housing is substantially equal to ambient pressure outside of the reservoir housing.

15. The device of claim 12, wherein the storage chamber and the dispensing chamber are in fluid communication with each other, and wherein a portion of the first fraction of the vaporizable material is drawn into the dispensing chamber in response to the dispensed vaporizable material being expelled from the dispensing chamber.

16. The device of claim 12, wherein the storage chamber and the dispensing chamber are separated by a reservoir barrier having at least one orifice extending therethrough, and wherein the at least one orifice is configured to allow a portion of the first fraction of the vaporizable material to be drawn into the dispensing chamber in response to the dispensed vaporizable material being expelled from the dispensing chamber.

17. The device of claim 12, wherein the first heating element is configured to selectively flash evaporate the dispensed vaporizable material into vaporized material in response to activation of the first heating element.

18. The device of claim 12, wherein the vaporization chamber defines an airflow passageway that extends therethrough, and wherein the airflow passageway is configured to allow the vaporized material to combine with an influx of air to substantially form an aerosol.

* * * * *